United States Patent
Van De Kerkhof et al.

(10) Patent No.: US 9,528,953 B2
(45) Date of Patent: Dec. 27, 2016

(54) THERMO-ANALYTICAL INSTRUMENT

(71) Applicant: Mettler-Toledo AG, Greifensee (CH)

(72) Inventors: Ernst Van De Kerkhof, Sittard (NL); Paul Pieter Willem Van Grinsven, Maasmechelen (BE)

(73) Assignee: Mettler-Toledo GmbH, Greifensee (CH)

( * ) Notice: Subject to any disclaimer, the term of this patent is extended or adjusted under 35 U.S.C. 154(b) by 254 days.

(21) Appl. No.: 14/168,778

(22) Filed: Jan. 30, 2014

(65) Prior Publication Data
US 2014/0146847 A1    May 29, 2014

Related U.S. Application Data (63) Continuation of application No. 12/694,464, filed on Jan. 27, 2010, now abandoned.

(30) Foreign Application Priority Data

Feb. 3, 2009 (EP) ..................... 09151986

(51) Int. Cl.
*G01N 25/00* (2006.01)
*G01N 25/20* (2006.01)
(Continued)

(52) U.S. Cl.
CPC ............... *G01N 25/20* (2013.01); *G01K 17/00* (2013.01); *G01K 17/04* (2013.01);
(Continued)

(58) Field of Classification Search
CPC  G01N 25/4866; G01N 25/4833; G01N 25/00; G01N 25/482; G01N 25/4826; G01K 17/00; G01K 17/04
(Continued)

(56) References Cited

U.S. PATENT DOCUMENTS 3,675,465 A    7/1972  Sommer et al.
5,335,993 A *  8/1994  Marcus ................. G01N 25/18
                                                           374/11
(Continued)

FOREIGN PATENT DOCUMENTS

CN    86108245 A    7/1987
CN    101109721 A   1/2008
(Continued)

OTHER PUBLICATIONS

Lagnier, R. et al., "The measurement of low temperature specific heats using dynamic differential calorimetry", Cryogenics, Jun. 1977, pp. 349-353, vol. 17, No. 6, Elsevier, Kidlington, Great Britain.

(Continued)

*Primary Examiner* — Lisa Caputo
*Assistant Examiner* — Jonathan Dunlap
(74) *Attorney, Agent, or Firm* — Standley Law Group LLP (57) ABSTRACT

A thermo-analytical instrument, especially a differential scanning calorimeter has a sample position (201, 401) for receiving a sample (206), a reference position (202, 402), a heating means associated with the sample position and the reference position, a means for setting a predetermined temperature program of nominal values of temperature versus time, a first sensor (407) for measuring a sample temperature ($T_S$) at the sample position, and a controller. The controller controls the heating power of the heating means so that measured sample temperature essentially follows the predetermined temperature program.

7 Claims, 5 Drawing Sheets

(51) Int. Cl.
*G01K 17/00* (2006.01)
*G01K 17/04* (2006.01)
*G01N 25/48* (2006.01)

(52) U.S. Cl.
CPC ..... *G01N 25/4833* (2013.01); *G01N 25/4866* (2013.01); *G01N 25/00* (2013.01); *G01N 25/482* (2013.01); *G01N 25/4826* (2013.01)

(58) Field of Classification Search
USPC .................................. 374/10, 11, 12, 29, 30
See application file for complete search history.

(56) References Cited

U.S. PATENT DOCUMENTS

| | | | |
|---|---|---|---|
| 5,346,306 A * | 9/1994 | Reading | G01N 25/18 374/10 |
| 5,549,387 A | 8/1996 | Schawe et al. | |
| 5,599,104 A | 2/1997 | Nakamura et al. | |
| 6,170,984 B1 | 1/2001 | Schawe et al. | |
| 6,402,369 B1 * | 6/2002 | Ludington | G01N 25/4866 136/204 |
| 6,428,203 B1 * | 8/2002 | Danley | G01K 17/00 374/1 |
| 6,508,585 B2 | 1/2003 | Nakamura et al. | |
| 6,632,015 B2 | 10/2003 | Nagasawa | |
| 6,913,383 B2 | 7/2005 | Jörimann et al. | |
| 7,021,820 B2 * | 4/2006 | Chippett | G01K 17/00 374/33 |
| 8,746,966 B2 * | 6/2014 | Van De Kerkhof | G01N 25/20 374/11 |
| 2005/0008063 A1 * | 1/2005 | Chippett | G01K 17/00 374/34 |
| 2005/0190813 A1 | 9/2005 | Schick | |
| 2006/0256836 A1 | 11/2006 | Hütter et al. | |
| 2010/0046573 A1 * | 2/2010 | Schick | G01K 17/04 374/11 |
| 2011/0013663 A1 | 1/2011 | Garden et al. | |

FOREIGN PATENT DOCUMENTS

| | | |
|---|---|---|
| DE | 202007002324 U1 | 6/2007 |
| EP | 0267308 A2 | 5/1988 |
| JP | 2006-105935 A | 4/2006 |
| JP | 2003-14674 A | 1/2013 |
| WO | 94/06000 A1 | 3/1994 |

OTHER PUBLICATIONS

Van Herwaarden, A.W., "Overview of calorimeter chips for various applications", Thermochimica Acta, 2005, pp. 192-201, vol. 432, Elsevier.

* cited by examiner

THERMO-ANALYTICAL INSTRUMENT

CROSS-REFERENCE TO RELATED APPLICATIONS

This application is a continuation of U.S. Ser. No. 12/694,464, filed 27 Jan. 2010, which makes claims priority under 35 USC §119 to European patent application 09 15 1986.8, which was filed 3 Feb. 2009. The content of both applications is incorporated by reference as if fully recited herein.

TECHNICAL FIELD

The disclosed embodiments relate to a thermo-analytical instrument utilizing an enhanced heat flux mode and to a method for operating such an instrument.

Thermo-analytical instruments are generally used to measure different characteristics and properties of a sample which is exposed to temperature changes and/or to a temperature program.

Well known examples for such thermo-analytical instruments are calorimeters and in particular differential scanning calorimeters (DSC). A DSC is utilized to record temperature related changes of the physical or chemical characteristics of a sample or sample material. These are for example heat flow measurements related to exothermic or endothermic events accompanying transitions and other effects occurring in a sample which is subjected to temperature changes. The changes within the sample are determined in relation to a reference, which can be an empty reference position or a suitable reference material. Depending on the type of DSC the reference material or sample material can be placed directly on a respective measurement position or it can be placed in a suitable crucible, which is then placed on the respective measurement position—the sample position or the reference position.

Chip-type calorimeters were developed for the analysis of very thin films and particles with masses in the microgram or even nanogram range, which are often based on silicon technology. An overview over different uses of these chip-type calorimeters, such as high-speed DSC, is given by A. W. van Herwaarden "Overview of Calorimeter Chips for Various Applications", Thermochimica Acta, 432 (2005), 192-201.

Two main control principles or modes for thermo-analytical instruments are well known, these are heat flux and power compensation.

Power compensation is usually implemented into a thermo-analytical instrument by controlling the heating power or by placing and separately controlling an additional heater, often referred to as compensation heater, at the sample position. The sample position, the reference position as well as any material placed on one of said measurement positions are subjected to a temperature program, which is applied by the respective heater to the respective measurement positions. The sample heater merely mimics the heating power delivered by the reference heater. Said compensation heater is used to deliver any excess power needed for heating the sample in order to take it through phase transitions, while the temperature difference between the sample position and the reference position is controlled to remain substantially zero.

The heat flux principle is often implemented in thermo-analytical instruments, such as calorimeters, having a common holder comprising the sample position and reference position. The holder is associated with a common heater, whose heating power is controlled by the temperature of the reference position. The thermal conductivity paths between the heater and the sample position and the reference position are well defined and heat flows calculated from the temperature signals of the sample and the reference can be quantitatively analyzed.

In the heat flux mode the heating power for the reference position and the sample position is controlled by the actual temperature at the reference position in accordance with the temperature program. Unfortunately, the sample temperature can divert substantially from the set program temperature and the sample temperature can be essentially non-linear with respect to time while the sample undergoes and/or relaxes from thermal events, especially when the relaxation is comparatively slow. Additionally, for the determination of the net sample heat flow all thermal properties have to be known with high accuracy, as this determination is generally very sensitive to inaccuracies in any of these properties. These drawbacks can lead e.g. to erroneous measurement results.

Therefore, it would be advantageous to develop a thermo-analytical instrument, in particular a thermo-analytical heat flux instrument, which overcomes the drawbacks of the heat flux principle described above and provides results having a higher reproducibility and accuracy.

The development of such a thermo-analytical instrument cannot be realized within the frame of the classic heat flux principle. The term 'classic' heat flux principle refers to the known principle. The basic principles concerning the heat flows when heating a reference position and the sample position under controlled conditions, e.g. inside a thermo-analytical instrument with heat flux are described in a generalized way with reference to FIG. 1. The reference position and the sample position are also referred to as 'measurement positions'.

Figure 1:
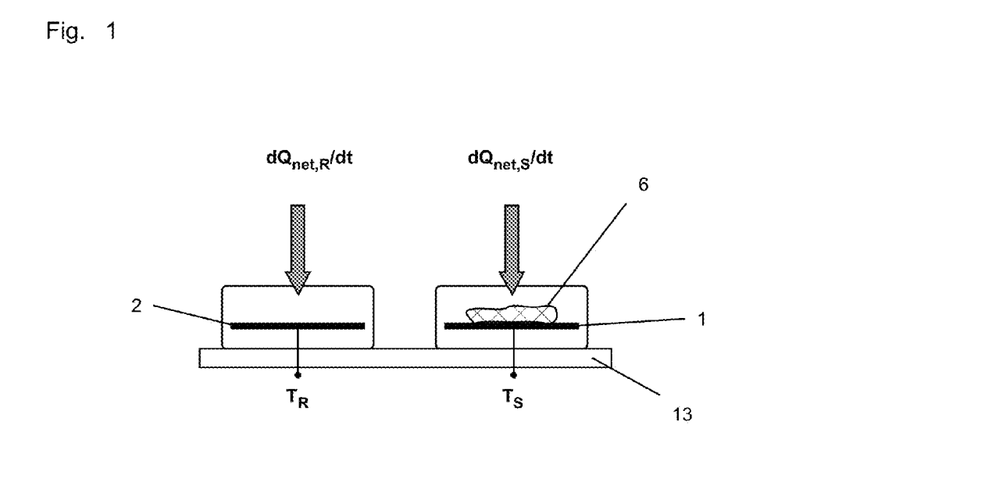
FIG. 1 is a simplified schematic representation of the heat flows in a thermo-analytical heat flux instrument.

FIG. 1 shows a schematic representation of a sample position 1 and a reference position 2, which are associated either with a common heater 13 or with individual heaters (not shown here). A sample 6 is arranged on the sample position 1 and the reference position 2 is preferably empty. For this situation all heat flows into and from the reference position 2 are added up into one net heat flow $dQ_{net,R}/dt \equiv \dot{Q}_{net,R}$. The net heat flow into the sample position 1 is represented by $\dot{Q}_{net,S}$. The temperatures at the reference position 2 and at the sample position 1 are $T_R$ and $T_S$, which are assumed to be uniform across the respective measurement position.

The energy balance at the sample position 1 requires that:

$$\dot{Q}_{net,S} = (C_S + m \cdot c_p) \cdot \dot{T}_S + \dot{q} \tag{1}$$

where $C_S$ denotes the heat capacity of the sample position, m the sample mass, $c_p$ the specific heat of the sample 6, in particular of the sample material, and $\dot{q}$ the heat flow into the sample 6 originating from a thermal event within the sample 6. Likewise, the energy balance for the reference position 2 can be expressed as:

$$\dot{Q}_{net,R} = C_R \cdot \dot{T}_R, \tag{2}$$

where $C_R$ is the heat capacity of the reference position.

For these calculations it is assumed, that the reference position 2 is empty and is not associated with any reference material. Nevertheless, it is in principle possible to use a reference material or substance.

Equations (1) and (2) can be subtracted to render $$\dot{Q}_{net,S} - \dot{Q}_{net,R} = (C_S + m \cdot c_p) \cdot \dot{T}_S - C_R \cdot \dot{T}_R + \dot{q} \tag{3}$$

The left hand side of Equation 3 represents the net heat flow imbalance between the measurement positions 1, 2 or in other words the incoming minus the outgoing heat flow, taken differentially between both measurement positions 1, 2. The left hand side contains contributions from the differences between the measurement positions 1, 2 in effectively applied heating power and/or thermal resistance to the environment and possibly from direct heat flow between sample position and reference position. The right hand side of Equation 3 represents the differential heat consumption rate between the measurement positions 1, 2, which originates from the intrinsic differential heat capacity or thermal imbalance between the two empty measurement positions 1, 2, the heat capacity of the sample 6 and from any thermal events occurring within sample 6.

Equation 3 can be solved for the net heat flow into the sample 6 to yield:

$$m \cdot c_p \cdot \dot{T}_S + \dot{q} = (C_R \cdot \dot{T}_R - C_S \cdot \dot{T}_S) + (\dot{Q}_{net,S} - \dot{Q}_{net,R}), \quad (4)$$

Depending on the actual setup, in particular the use of a common heater 13 or individual heaters for the measurement positions 1, 2, $\dot{Q}_{net,S}$ and $\dot{Q}_{net,R}$ contain contributions from heat flows between the heater 13 and the measurement positions 1, 2, between the measurement positions 1, 2 and the thermal environment and/or mutually between the sample position 1 and the reference position 2. Most commonly each of these terms can be represented as a heat flow across a thermal resistance, driven by a differential temperature. Provided all thermal resistances and temperatures involved are well-defined, quantitative results can be obtained for the differential heat flow term $\dot{Q}_{net,S} - \dot{Q}_{net,R}$ in Equation 4, although in practice small errors in these thermal properties can result in large relative inaccuracies in the net heat flow signal.

The reference temperature $T_R$ is controlled to follow a predetermined temperature program, when implementing the classic heat flux principle into a thermo-analytical instrument. This temperature program can for instance consist of time segments during each of which $T_R$ stays at a constant value—is isotherm—or varies linearly with time.

Therefore, its temporal derivative $\dot{T}_R$ is time independent, at least within one program segment, and Equation 3 can be rewritten as:

$$\dot{Q}_{net,S} - \dot{Q}_{net,R} = (C_S + m \cdot c_p)\frac{d(\Delta T)}{dt} + (C_S + m \cdot c_p - C_R) \cdot S + \dot{q}, \quad (5)$$

wherein $S = \dot{T}_R$ denotes the scan rate and $\Delta T = T_S - T_R$ the differential temperature between the measurement positions 1, 2.

Under non-extreme conditions it can be assumed, that the differential heat capacity $|C_S - C_R|$ is small compared to the thermal mass $m \cdot c_p$ of the sample, so that the net heat flow in Equation 5 can be further reduced to:

$$\dot{Q}_{net,S} - \dot{Q}_{net,R} = (C + m \cdot c_p)\frac{d(\Delta T)}{dt} + m \cdot c_p \cdot S + \dot{q} \quad (6)$$

with $C_R \cong C_S \equiv C$
or, when solved for the net heat flow:

$$m \cdot c_p \cdot S + \dot{q} = -(C + m \cdot c_p)\frac{d(\Delta T)}{dt} + (\dot{Q}_{net,S} - \dot{Q}_{net,R}) \quad (7)$$

Assuming a substantially uniform heater and/or environment temperature, as well as basic symmetry between the thermal resistances connecting the sample position 1 and the reference position 2 to their respective thermal environments, the net heat flow term in Equation 7 will be dominated by a term proportional to the temperature difference $\Delta T$ between the measurement positions 1, 2. This implies, that under steady-state conditions, when $\dot{q}$ is substantially zero, without occurrence of any additional thermal event, and after relaxation of entrance effects, $\Delta T$ will remain at a substantially constant value.

The value of $\Delta T$ can be approximated by $$\Delta T \approx -Z \cdot m \cdot c_p \cdot S \quad (8)$$

with Z being the effective thermal resistance between the sample position and the reference position, which will be a function of the various contributing thermal resistances.

The differential temperature $\Delta T$ will vary during any thermal event occurring within sample 6, causing further discrepancy between the sample temperature $T_S$ and the set program temperature. Additionally, this will induce nonlinearity into the time dependence of the sample temperature $T_S$. After the thermal event, when $\dot{q}$ has returned to substantially zero, $\Delta T$ will relax to its steady-state value (s. Equation 8) in an exponential decay with a time constant $$\tau \approx Z \cdot (C + m \cdot c_p) \quad (9)$$

The total transition enthalpy for the thermal event occurring within sample 6 can be given by:

$$\int_{t_0}^{t_1} \dot{q} \, dt = \quad (10)$$

$$\int_{t_0}^{t_1} \left\{ -m \cdot c_p \cdot S - (C + m \cdot c_p)\frac{d(\Delta T)}{dt} + (\dot{Q}_{net,S} - \dot{Q}_{net,R}) \right\} dt$$

The integration runs from $t=t_0$, a point in time prior to the onset of the thermal event, to $t=t_1$, when steady-state conditions have been restored after relaxation from the thermal event. Let $T_0$ and $T_1$ be the set program temperatures at $t=t_0$ and $t=t_1$. With the assumption that $c_p(T)$ is constant for $T_0 < T < T_1$ the integral of Equation 10 can be partly evaluated to yield:

$$\int_{t_0}^{t_1} \dot{q} \, dt = \int_{t_0}^{t_1} \{\dot{Q}_{net,S} - \dot{Q}_{net,R}\} dt - \quad (11)$$
$$\text{—Term 1—}$$
$$m \cdot c_p \cdot (T_1 - T_0) - (C + m \cdot c_p) \cdot (\Delta T_1 - \Delta T_0)$$
$$\text{-Term 2-} \qquad \text{—Term 3—}$$

Term 1 of Equation 11 gives the area under the curve, Term 2 the area under the interpolated baseline and Term 3 is the error term. Under ideal conditions, assuming that all properties are measured instantaneously with infinite precision, plotting the integrand from Term 1 against time will lead to a curve which is a horizontal straight line interrupted by the transition peak, except for the contribution from the Error Term 3. The Error Term 3 vanishes if $\Delta T_0 \approx \Delta T_1$. Under this condition the transition enthalpy of the sample can be determined as the area between the curve and the interpolated baseline.

Unfortunately experimental conditions are usually far away from the ideal conditions described above. Under experimental conditions, even after complete relaxation, $\Delta T_0 \neq \Delta T_1$, and therefore the error term always has to be considered and cannot be neglected. Furthermore, the net heat flow term in Equation 11 involves subtraction of numbers of nearly equal magnitudes, which is therefore critically dependent on the accuracy by which the underlying expressions and properties can be determined. As a consequence of these cumulative sources of inaccuracy, the resulting plots show a baseline drift and a curvature, which can only be corrected for by empirical means.

During a classic heat flow experiment the sample temperature is lagging behind the reference temperature and therewith the program temperature, so that a thermal lag as well as a time lag between the actual sample temperature and the reference temperature can occur.

In summary, realizing a thermo-analytical instrument with classic heat flow has several drawbacks, as the instrument will suffer from inevitable real-world limitations. The sample temperature $T_S$ can divert substantially from the given program temperature. The time derivative of the sample temperature $D_S$ is essentially non-constant during and while relaxing from a thermal event within the sample. The relaxation from thermal events is slow in comparison with an instrument using power compensation and the determination of the net sample heat flow is sensitive to inaccuracy in the measured and predetermined thermal properties.

These drawbacks become even more enhanced for small scale thermo-analytical instruments, such as e.g. chip-type calorimeters and DSC.

Additionally, thermo-analytical instruments are generally either designed for power compensation mode or heat flux mode, so that different instruments are necessary in order to support the two principles or modes. It would therefore also be advantageous to develop an instrument which could switch between power compensation mode and heat flux mode.

For power compensation it is essential that the sample position and the reference position are thermally separated. Heat flow measurements can in principle be carried out using thermally separated measurement positions, as long as the thermal conductivity paths between the reference position, the sample position and the surroundings are well defined.

The realization of the heat flux principle with a thermo-analytical instrument comprising thermally separated measurement positions also generates several drawbacks, which get more enhanced with decreasing sample sizes. After all, in the absence of a direct heat flow between the sample position and the reference position, the heat flow signal originates from subtracted bulk heat flows into and out of the measurement positions. The smaller the sample, the closer together these bulk heat flows will be, making the heat flow signal increasingly sensitive to errors and/or inaccuracies in the bulk heat flows.

An object lies in the development of a setup for an improved heat flux principle, which eliminates or at least reduces the impact of the drawbacks of classic heat flux principle as described above.

SUMMARY

This objective is achieved by a thermo-analytical instrument, in particular a differential scanning calorimeter, comprising a sample position for receiving a sample, a reference position, heating means associated with the sample position and the reference position, means for setting a predetermined temperature program of nominal values of temperature versus time, a first sensor for measuring a sample temperature at the sample position, and further comprising a controller, which controls the heating power of said heating means. The heating power of said heating means is controlled so as to cause said measured sample temperature to essentially follow said temperature program.

For a classic heat flux instrument the heating power would rather be controlled by the measured reference temperature or by the temperature of the heating means giving rise to the drawbacks described above. Offering the temperature program to the sample position and controlling the heating power through the actual or measured sample temperature substantially eliminates the deviation of the sample temperature from the set program temperature. This element of enhanced heat flow represents a kind of active sample control. The heat flux principle or mode according to the described embodiments will be referred to as 'enhanced' heat flow in order to differentiate it from the known or "classic" heat flow.

During an experiment the reference temperature is speeding ahead of the sample temperature in a mirror image of the classic reference controlled situation, but unlike classic heat flow a diversion of the reference temperature from the set program temperature does not influence the relation between the sample temperature and the set program temperature, which leads to a drastic lag reduction.

Further the direct control of the sample temperature also results in increasing the rising edge steepness during an event. In the classic heat flux mode the rate at which heat is delivered to the sample is limited by the substantially constant thermal resistance between the sample position and the reference position, which puts a rigid constraint on the heat flow between the sample position and the reference position. In the enhanced heat flux mode the sample is actively dragged through its phase transition by the controller, which is especially advantageous for samples having higher thermal masses in relation to an imbalance in thermal mass between the sample position and the reference position.

The thermo-analytical instrument further comprises a second sensor for measuring a reference temperature at the reference position. The temperature difference, i.e. a differential temperature, arising between the sample position and the reference position can be determined and can also represent a measuring signal. For example the sensor can comprise a thermopile arrangement with at least one thermocouple associated with the sample position and at least one thermocouple associated with the reference position for determining the temperature at the respective measurement position. It is also possible that the sample position and the reference position are associated with individual thermopile arrangements. The temperature at the respective measurement position can also be determined by other commonly known temperature measurement devices or sensors, for example a resistance thermometer or a semiconductor based sensor.

Preferably the reference position is empty, but in an exemplary embodiment the reference position can also be associated with a suitable reference substance or material. This is advantageous for certain experimental situations such as cooling experiments.

The heating means can comprise a common heater associated with the sample position and the reference position or the heating means can comprise individual heaters—a reference heater associated with the reference position and a sample heater associated with the sample position.

In an exemplary embodiment the measurement positions are designed in such a way that the thermal crosstalk between the sample position and the reference position is small or can even be neglected, this is especially advantageous as it allows combining the principles of enhanced heat flux and power compensation in a single thermo-analytical instrument.

Preferably, the heaters are resistance heaters, as these are particular suitable for instruments for small sample sizes and masses. Besides resistance heaters it would also be possible to use any other kind of heater, especially such which have been or are already used for thermo-analytical instruments, e.g. inductive heaters or laser heating.

The sample position and the reference position can be arranged on a common holder or they can be arranged on individual or separate holders. A holder is understood in this context as a substrate or structure on which the respective measurement positions are arranged or formed. A thermo-analytical instrument with individual holders is especially suited for instruments which can switch between heat flux and power compensation, as both principles can be utilized. Besides the arrangement on a common holder or on individual holders, the measurement positions can also be arranged in the same or in different environments, such as common or individual furnaces or sensors.

It is further advantageous that the sample position and the reference position exhibit an intrinsic symmetry in order to keep the imbalance in thermal mass between the sample position and the reference position at a minimum. Additionally, a low thermal inertia of the sample position and the reference position is important for the realization of the enhanced heat flow, for the system has to be able to respond swiftly, in relation to the time scale of the experiment, to the possibly large fluctuations in heating power during thermal events occurring in the sample.

In an exemplary embodiment the thermo-analytical instrument is a heat flux calorimeter operated under isoperibolic conditions. In an isoperibolic calorimeter, the temperature of the surroundings remains constant, while the temperature of the sample can differ from the surrounding temperature. In an exemplary embodiment the thermo-analytical instrument is designed as a differential scanning calorimeter, e.g. a chip-type calorimeter. These types of instruments are just examples of possible instruments. The thermo-analytical instrument can be any type of instrument with at least a sample position and a reference position. Classic heat flow was realized for example with differential scanning calorimeters (DSC) and thermo-analytical instruments combining DSC and thermo-gravimetric analysis (TGA). These and related instruments can also be realized with enhanced heat flow.

The enhanced heat flux principle can be applied when the time constant involved in transferring heat from the heater to a sample arranged at the sample position is low enough to prevent large gradients from arising during a thermal event occurring in the sample.

The enhanced heat flux mode has several advantages over the classic heat flux mode where the sample temperature runs behind the program temperature. For example the classic heat flux mode causes a delay of the onset of the phase transition peak for a heating or cooling scan of a sample material undergoing a first order phase transition and further a prolonged spell of non-linearity in the sample temperature can occur. The enhanced heat flux mode eliminates both effects and the lag can be substantially reduced, ideally it can be substantially zero. Furthermore, for the classic heat flux principle the steepness of the onset part or rising edge of the peak is generally limited by the overall heating rate. For the enhanced heat flux principle this is not the case. The enhanced heat flux principle produces a steeper edge, which results in a narrower peak and less delay of the peak temperature. Finally, relaxation is also faster for the enhanced principle, which further contributes to a narrow peak.

A method for controlling a thermo-analytical instrument with a sample position for receiving a sample, a reference position, heating means associated with the sample position and the reference position, means for setting a predetermined temperature program of nominal values of temperature versus time, a first sensor for measuring a sample temperature at the sample position, and a controller, which controls the heating power of said heating means, comprises the steps of placing a sample on the sample position, applying the predetermined temperature program to the sample position and the reference position by controlling a heating power of the heating means and determining the sample temperature as a function of time. The measured sample temperature can then be used to control the heating power of said heating means so as to cause said measured sample temperature to essentially follow said predetermined temperature program.

Preferably the thermal mass of the sample is always high compared to the imbalance in thermal mass between reference position and the sample position.

The heating means can comprise a common heater associated with the sample position and the reference position or it can comprise individual heaters—a reference heater associated with the reference position and a sample heater associated with the sample position.

The net heat flow into the sample can be derived from measuring the differential temperature arising between the sample position and the reference position. Imbalances between the measurement positions in effective heating power and/or heat flow to the environment can also contribute to the net heat flow into the sample.

Because of the active control through the sample temperature the sample and program temperatures are substantially identical and therefore the principal component of thermal lag can be eliminated.

Further and foremost, with respect to the equations presented above, S now represents the time derivative of the sample temperature $T_S$ rather than of the reference temperature $T_R$, implying that the sample temperature $T_S$ varies linearly with time. It follows from this, that time and sample temperature axes are fully proportional and can be freely interchanged.

Further, the time constant for relaxation from a thermal event has dropped from $Z \cdot (C+m \cdot c_p)$ to $Z \cdot C$, resulting in a faster exponential decay back to the baseline after a thermal event, a difference which becomes more pronounced for samples with a relatively large thermal mass with respect to the thermal mass of the sample position. The relaxation time is now determined by the reference position instead of the sample position. This results in an improved system response because of the absence of the additional inertia contributed by the sample.

A further advantage of the enhanced heat flux principle is that the peak height-to-width ratio is improved by virtue of two separate mechanisms. Onset steepness increases because of the active sample control, while the relaxation time decreases because the ruling time constant is that of the preferably empty reference position rather than of the sample position.

BRIEF DESCRIPTION OF THE DRAWINGS

The disclosed embodiments are described in more detail below with reference to the following figures. Thermal resistances are represented by the symbol Z to avoid confusion with electrical resistances R. In the figures.

DETAILED DESCRIPTION OF A PREFERRED EMBODIMENT

FIG. 1 as described in detail above shows a schematic representation of the heat flows in a heat flux thermo-analytical instrument. The reference position and the sample position are also referred to as "measurement positions."

Figure 2:
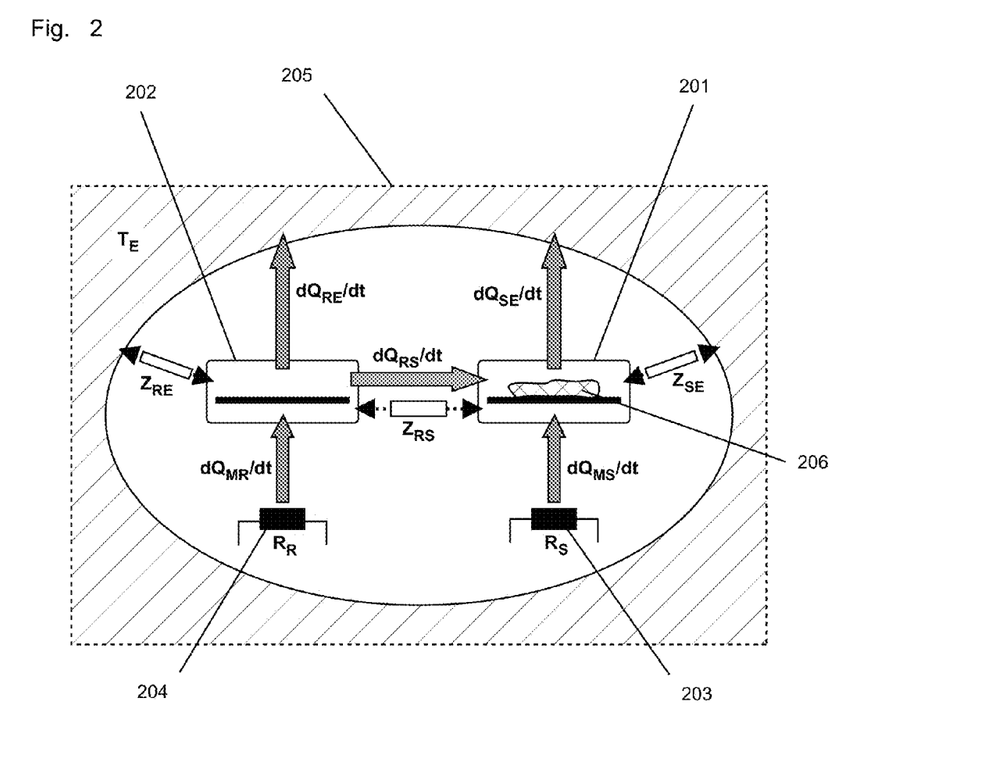
FIG. 2 schematically represents the heat flows in a heat flux thermo-analytical instrument having substantially symmetric measurement positions and individual heaters for the sample position and the reference position.

FIG. 2 schematically shows the heat flows within a thermo-analytical instrument 205. The thermo-analytical instrument 205 comprises a sample position 201, a reference position 202, a sample heater 203 and a reference heater 204. The sample position 201, the reference position 202 and the heaters 203, 204 are comprised in the thermo-analytical instrument 205, which is only indicated here and which also represents the surrounding environment, presumed to remain at a uniform temperature $T_E$. The thermo-analytical instrument 205 is preferably operated under isoperibolic conditions and has substantially symmetric measurement positions 201, 202 with individual heaters 203, 204.

An example for an instrument for which the heat flows can be modeled by FIG. 2 is a chip-type differential scanning calorimeter with individual heaters.

The various heat flows are indicated by arrows for the situation when a sample 206 is arranged on the sample position 201 and the respective heaters 203, 204 provide heating power to both measurement positions 201, 202 according to a common, predetermined temperature program. The predetermined temperature program can also be a voltage program, in particular when the heaters 203, 204 are resistance heaters. The heaters 203, 204 can be designed as electrical resistance heaters, which deliver heating power to the respective measurement positions 201, 202. The heating powers of the two heaters 203, 204 are not necessarily equal, even when the heaters 203, 204 are subjected to exactly the same voltage program, because the heating power is inversely proportional to the electrical heater resistance, which is significantly temperature dependent. Since the temperature difference between the measurement positions 201, 202 can become quite substantial during thermal transitions in the sample, this effect can by no means be ignored.

For calculating the heat flow in the sample 206 all heat flows shown in FIG. 2 have to be taken into account. In order to avoid confusion with electrical resistances R the thermal resistances have been given the symbol Z. The terms are further characterized by indices S, R, H and E representing Sample position, Reference position, Heater and Environment. $\dot{X}$ marks the temporal derivative of the term $\dot{X}=dX/dt$. The energy balance at the sample position 201 requires according to Equation 1 that:

$$\dot{Q}_{net,S} = \dot{Q}_{HS} + \dot{Q}_{RS} - \dot{Q}_{SE} = (C_S + m \cdot c_p) \cdot \dot{T}_S + \dot{q} \tag{1a}$$

$$\text{with } \dot{Q}_{HS} = \frac{U_H^2}{R_S}, \dot{Q}_{RS} = \frac{T_R - T_S}{Z_{RS}} \text{ and } \dot{Q}_{SE} = \frac{T_S - T_E}{Z_{SE}}.$$

$\dot{Q}_{HS}$ is the heat generated per time unit by the sample heater 203, which flows to the sample position 201. $\dot{Q}_{RS}$ is the heat flow from the reference position 202 to the sample position 201 and $\dot{Q}_{SE}$ the heat flow from the sample position 201 to the environment 205. $C_S$ denotes the heat capacity of the sample position, m the mass and $c_p$ the specific heat of the sample 206, in particular of the sample material. $T_S$ is the temperature at the sample position 201 and is assumed to be equal to the temperature of the sample 206. $\dot{q}$ is the heat flow into the sample 206 originating from a thermal event within the sample 206. $T_R$ denotes the temperature at the reference position 202, $T_E$ the temperature of the environment 205, $U_H$ the voltage applied to the heaters 203, 204 of the measurement positions 201, 202, $R_S$ the electrical resistance of the sample heater 203, and $Z_{RS}$, $Z_{SE}$ denote the thermal resistances between the measurement positions 201, 202 and between the sample position 201 and the environment 205, respectively.

Likewise, the energy balance for the reference position 202 can be expressed according to Equation 2 as:

$$\dot{Q}_{net,R} = \dot{Q}_{HR} - (\dot{Q}_{RS} + \dot{Q}_{RE}) = C_R \dot{T}_R, \tag{2a}$$

$$\text{with } \dot{Q}_{HR} = \frac{U_H^2}{R_R} \text{ and } \dot{Q}_{RE} = \frac{T_R - T_E}{Z_{RE}}.$$

$\dot{Q}_{HR}$ is the heat generated by time unit by the reference heater 204 and $\dot{Q}_{RE}$ the heat flow from reference position 202 to the environment 205. $C_R$ is the heat capacity and $T_R$ the temperature of the reference position 202. $R_R$ denotes the electrical resistance of the reference heater 204 and $Z_{RE}$ the thermal resistance between the reference position 202 and the environment 205.

For these calculations it is assumed, that the reference position 202 is empty and is not associated with any reference material. Nevertheless, it is in principle possible to use a reference material.

It is advantageous, when the thermal crosstalk between the measurement positions 201, 202 is minimized. This can be achieved for thermally separated measurement positions, as described with regard to FIG. 2.

The thermal crosstalk can be neglected, if it is small. Otherwise the actual thermal crosstalk should be considered and can be determined experimentally for a given thermo-analytical instrument 205 by comparing cooling and heating runs, where respective runs show opposite signs for said effect. First thermal imbalances between the measurement positions can be determined with measurement positions which are empty for the cooling and heating runs. Advantageously, these measurements show no significant asymmetry between the heating and cooling runs, implying that the actual thermal imbalance between sample position and reference position is negligibly small. Once this quantity is known the experiment can be performed for a sample material with a known thermal mass and an empty reference position. The measured thermal mass, after correction for the intrinsic difference between both empty positions, can be determined and compared with the known mass. Any difference in the measured thermal mass between heating and cooling runs is an indication for thermal crosstalk.

Under the assumption that the thermal crosstalk is negligible these equations can be solved analogue to Equations 3 to 11 described above, by making the following substitution:

$$\dot{Q}_{net,S} - \dot{Q}_{net,R} \rightarrow U_H^2 \left( \frac{1}{R_S} - \frac{1}{R_R} \right) - \left( \frac{T_S - T_E}{Z_{SE}} - \frac{T_R - T_E}{Z_{RE}} \right) \quad (12)$$

Equations 8 and 9 remain unchanged as first order approximations, although Z now represents the thermal resistance between the measurement positions and the environment, averaged between the sample position and the reference position and disregarding the contribution from the electrical term. In particular with a chip-type calorimeter it has to be observed that in a realistic setup, using classic heat flow, the temperature difference between the sample temperature $T_S$ and the given or predetermined program temperature $T_{set}$ can easily amount to several tens of degrees, as can be calculated exemplarily with Equation 8 using realistic values of $Z=0.5-1\times10^4$ K/W under air/nitrogen and $m\cdot c_p \cdot S=10^{-8}-10^{-2}$ K/s.

Further all mathematical operations, in particular the subtractions, are critically dependant on the accuracy by which the individual properties can be determined. This is particularly important with respect to the thermal resistances Z. The thermal resistances Z cannot be determined directly, but have to be calculated from properties which are determined during a calibration of the instrument. In particular in a calorimeter under isoperibolic conditions, e.g. in a chip-type calorimeter, any sample arranged on the sample position has an impact on the thermal resistance $Z_{SE}$ of the sample position to the environment, which has to be accounted for. Further, several assumptions and simplifications have been made in relation to the calculations for classic heat flow, which all are to some extent invalid, especially the farther the system is away from ideal conditions. These assumptions included e.g. a constant value for the heat capacity $c_p$, equal heat capacities of the empty measurement positions and in case of a chip-type calorimeter the geometrical stability of the sample. As the experimental conditions can vary substantially from the ideal conditions, the resulting plots show a baseline drift and a curvature, which can only be corrected for by empirical means.

A chip-type calorimeter represents an example of a suitable thermo-analytical instrument, which can comprise thermally separated measurement positions. Especially when implemented on a microscale—like in a chip-type calorimeter—a setup as described above is more susceptible to the aforementioned drawbacks of classic heat flow. Therefore the implementation of the enhanced heat flow as described herein is especially advantageous.

Figure 3:
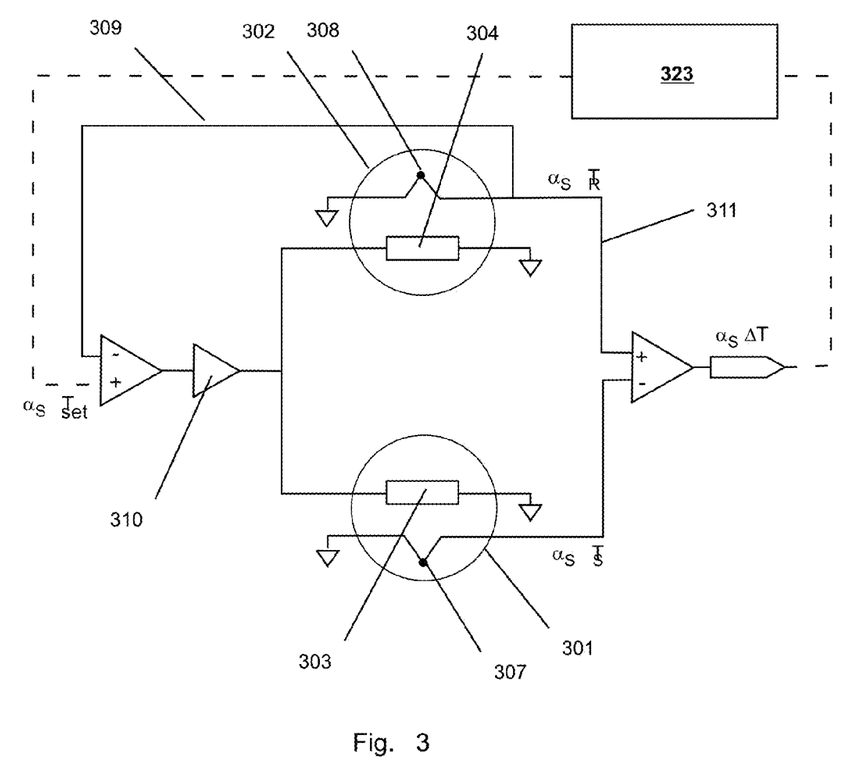
FIG. 3 depicts an electronic setup for a digital scanning calorimeter ("DSC") with classic heat flow.

FIG. 3 shows an electronic setup of a thermo-analytical instrument such as a DSC operated with the classic heat flux principle.

The DSC presented in FIG. 3 comprises a sample position 301 and a reference position 302. A sample or sample material can be placed on the sample position 301 and a reference material can be placed on the reference position 302. Preferably measurements are performed without a reference material.

The sample position 301 is in thermal contact with a sample heater 303. The temperature at the sample position 301 is determined by a sensor comprising a thermopile 307 with at least one thermocouple. Likewise the reference position 302 is in thermal contact with a reference heater 304. The temperature at the reference position 302 is determined with a sensor comprising a thermopile 308 with at least one thermocouple. The heaters 303, 304 are preferably designed as individual resistance heaters, which can be controlled by the same temperature or voltage program. The sample heater 303 and the reference heater 304 apply a heating power to the measurement positions 301, 302 in compliance with a predetermined temperature program and are part of a control loop 309. This control loop 309 comprises a PID controller 310. The temperature program is fed to the control loop 309 as indicated by the temperature set points $T_{set}$. $\alpha_S T_{set}$ is the product of the temperature $T_{set}$ with the Seebeck coefficient $\alpha_S$ and converts the temperature into voltage, provided $T_S$ is measured relative to the temperature of the cold junctions of the thermopile. The heating power of the heaters 303, 304 is controlled by the temperature $T_R$ at the reference position 302, which is determined with the thermopile 308.

The sensors comprising the thermopiles 307, 308 are part of a measurement circuit 311, whose output is a differential thermopile signal derived from the two thermopiles 307, 308. Here the differential thermopile signal directly represents the measured signal.

The control loop 309 as well as the measurement circuit 311 are connected with a main controller 323, in particular a microcontroller, for controlling the DSC.

Figure 4:
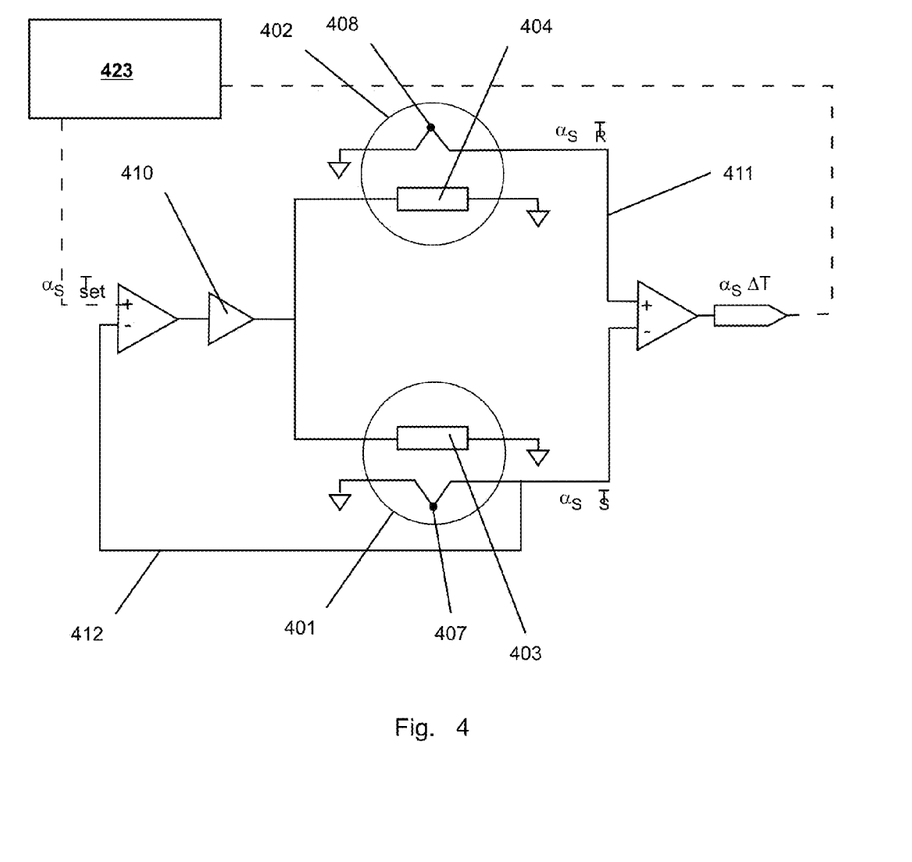
FIG. 4 depicts an electronic setup for a DSC with enhanced heat flow.

FIG. 4 shows an electronic setup for a DSC as example for a thermo-analytical instrument with enhanced heat flux principle. The thermo-analytical instrument also comprises a sample position 401, a sample heater 403 associated with the sample position 401 and a first temperature sensor comprising a first thermopile 407 with at least one thermocouple for measuring the temperature at a sample position 401. The instrument further comprises a reference position 402 associated with a reference heater 404 and a second temperature sensor comprising a second thermopile 408 with at least one thermocouple for measuring the temperature at the reference position 402. The sample heater 403 and the reference heater 404 apply a heating power to the respective measurement position 401, 402 in compliance with a predetermined temperature program and are part of a control loop 412. This control loop 412 comprises a PID controller 410. The predetermined temperature program is fed to the control loop 412 as indicated by the temperature set points $T_{set}$.

The sensors comprising the thermopiles 407, 408 are part of a measurement circuit 411, whose output is a differential thermopile signal derived from the two thermopiles 407, 408. The differential thermopile signal can again represent the measured signal.

The control loop 412, as well as the measurement circuit 411, is connected with a main controller 423, in particular a microcontroller, for controlling the DSC.

So far the enhanced heat flux principle is very similar to the classic heat flux principle. The main difference is that the heating power of the heaters 403, 404 is controlled by the temperature $T_S$ at the sample position 401, which is determined with the thermopile 407, rather than the temperature $T_R$ at the reference position 402. The measure of offering the temperature program to the sample position 401 substantially eliminates the deviation of the sample temperature $T_S$ from the given program temperature $T_{Set}$ and presents a substantive advantage over the classic heat flux principle.

The enhanced heat flux principle is applicable only when the time constant involved in transferring heat from the sample heater 403 to a sample arranged at the sample position 401 is low enough to prevent large gradients from arising during a thermal event, which is e.g. the case for a so called chip-type calorimeter.

Both setups shown in FIGS. 3 and 4 can easily be adapted by adding a compensation heater to each measurement position and by connecting the compensation heaters into an appropriate compensation loop which is fed by the differential temperature arising between the measurement positions. With these adaptations the resulting instrument is capable of performing either in one of the heat flux modes or in a power compensation mode, which can be a classic or an enhanced power compensation mode analogue to the heat flux modes.

Figure 5:
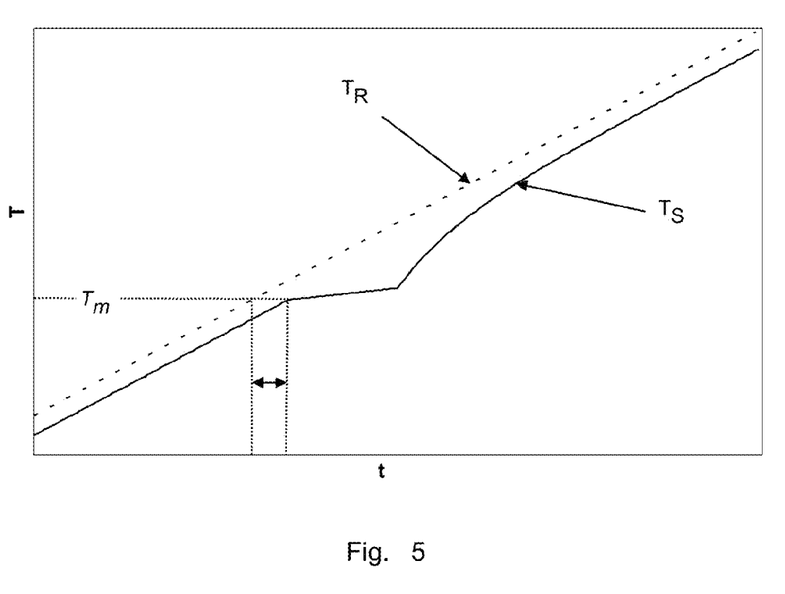
FIG. 5 is a temperature-time-diagram for the setup according to FIG. 3 during a thermal event.
Figure 6:
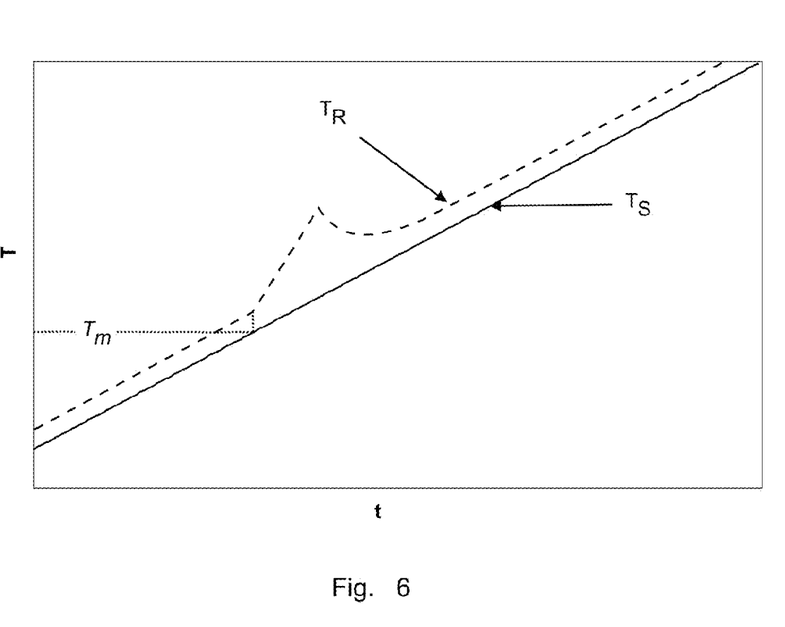
FIG. 6 is a temperature-time-diagram for the setup according to FIG. 4 during a thermal event.

FIGS. 5 and 6 show idealized graphs of temperature T versus time t during a linear heating scan, within which the sample goes through an endothermic first order phase transition. The reference temperature $T_R$ is represented as a dotted line, the sample temperature $T_S$ as a straight line.

FIG. 5 displays the situation for the classic heat flux principle, where the temperature program $T_{set}$ is applied according to the measured reference temperature $T_R$. FIG. 6 displays the situation for the enhanced heat flux principle with active control of the temperature program $T_{set}$ through the sample temperature $T_S$.

For the classic heat flux mode the sample temperature $T_S$ runs behind the program temperature $T_{set}$ throughout the scan, causing a delay of the onset of the melting peak, which is derived from the differential temperature signal. This delay is represented by the double arrow in FIG. 5. During and after the transition a prolonged spell of non-linearity in the sample temperature $T_S$ occurs. It is evident from FIG. 6, that both effects are absent in the sample temperature graph with the enhanced heat flux principle, where the lag is substantially reduced and is ideally substantially zero. Furthermore, for the classic heat flux principle the steepness of the onset part or rising edge of the peak is limited by the overall heating rate (FIG. 5). For the enhanced heat flux principle this is not the case. It is evident from FIG. 6, that the enhanced heat flux principle produces a steeper edge, which results in a narrower peak and less delay of the peak temperature. Finally, relaxation is also faster for the enhanced principle, which further contributes to the narrow peak.

The heat flow analysis performed for the classic heat flux principle can now be adjusted to describe the enhanced heat flux principle, thereby showing the implications for and the advantages of the principle taught herein.

Starting from Equation 4, treating the rate of change of the sample temperature as constant $\dot{T}_S = S$ and assuming equal heat capacities for the empty measurement positions, the following equation is obtained:

$$m \cdot c_p \cdot S + \dot{q} = -C \frac{d(\Delta T)}{dt} + (\dot{Q}_{net,S} - \dot{Q}_{net,R}) \tag{13}$$

At a first glance, Equation 13 appears to be quite similar to its counterpart, Equation 7, for the classic heat flux principle. However, there are some vital differences, bringing forth beneficial effects. The sample and program temperatures are substantially identical by which the principal component of thermal lag is eliminated.

Further and foremost, S now represents the time derivative of the sample temperature $T_S$ rather than the reference temperature $T_R$, implying that the sample temperature $T_S$ varies linearly with time. It follows from this, that time and sample temperature axes are fully proportional and can be freely interchanged.

Further, the time constant for relaxation from a thermal event has dropped from $Z \cdot (C + m \cdot c_p)$ to $Z \cdot C$ for an experiment without a reference material, resulting in a faster exponential decay back to the baseline after a thermal event, a difference which becomes more pronounced for samples with a relatively large thermal mass. The relaxation time is now determined by the reference position instead of the sample position resulting in an improved system response due to the absence of the additional inertia contributed by the sample. Preferably, experiments are carried out without a reference material. However, a combination of a high cooling rate and a large thermal sample mass might induce a substantial temperature difference between the sample position and the reference position and thereby, since the reference temperature is running ahead of the program temperature, reduce the temperature range over which controlled cooling is possible. For these cases the use of a reference material is preferred to counteract this phenomenon.

By integration of Equation 13 the transition enthalpy can be calculated, under the assumption of a constant $c_p$:

$$\int_{t_0}^{t_1} \dot{q} \, dt = \tag{14}$$

$$\int_{t_0}^{t_1} \{\dot{Q}_{net,S} - \dot{Q}_{net,R}\} dt - m \cdot c_p \cdot (T_1 - T_0) - C \cdot (\Delta T_1 - \Delta T_0)$$

This expression is nearly identical with the enthalpy calculated for the classic heat flux principle according to Equation 11, except for the error term, which is noticeably smaller. The error term is smaller as C is smaller than $(C + m \cdot c_p)$ and because the sample transition is completed over a narrower temperature interval. Therefore, the temperature dependence of $\Delta T$ will act over a smaller range causing $\Delta(\Delta T)$ to become smaller on average. The temperature dependence exists due to intrinsic as well as sample induced imbalances between the reference position and the sample position.

Aside from the error term being smaller, the fact that $t_0$ and $t_1$, as well as $T_0$ and $T_1$, are closer together improves the accuracy, for it will reduce the influence of variability of c, and limit the range over which the properties in the integrand inside the brackets need to be known with high precision.

Figure 7:
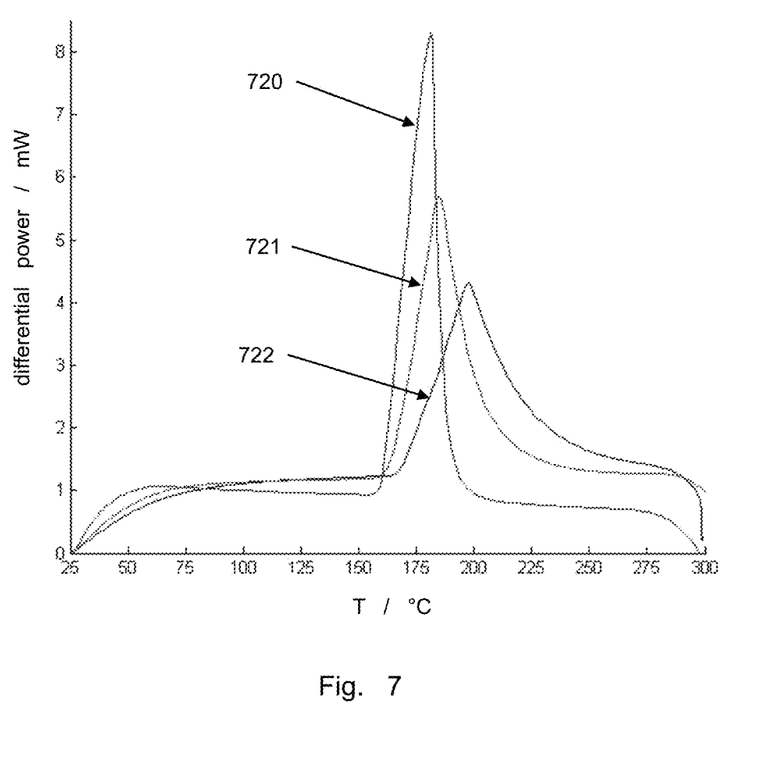
FIG. 7 is a diagram of the differential power versus time for comparative measurements of the melting peak of indium (5 μg, 1000 K/s) with power compensation, classic heat flow and enhanced heat flow.

In FIG. 7, three comparative measurements are presented, placing the enhanced heat flow 721 right in the middle between classic heat flow 722 and power compensation 720, although the enhanced heat flow figures are closer to power compensation 720 than to classic heat flow 722. It can be observed, that the enhanced heat flow comprises elements from both principles and at the same time reduces and/or eliminates their drawbacks substantially.

The enhanced heat flow gives rise to an increased responsibility of the main control loop when pulling the sample through phase transitions and places higher demands on its stability. Therefore, the use of a robust temperature control, such as a PID-control, is preferably required.

Exemplary comparative calorimetric measurements for the three different calorimetric methods showed, that within an error margin of a few percent, the enthalpy of fusion of a given indium sample, as measured for three different heating rates, does not show any significant dependence on the method used and neither on the heating rate. This confirms that measurements with the enhanced heat flux principle are calorimetrically reliable as much as measurements with classic heat flux and power compensation.

What is claimed is:

1. A method for operating a thermo-analytical instrument in an enhanced heat flux mode, the thermo-analytical instrument comprising a sample position and a reference position, means for heating each of the sample position and the reference position, sample temperature sensing means for sensing a temperature of a sample placed at the sample position, reference temperature sensing means for sensing a temperature at the reference position, and means for controlling the power supplied by the means for heating to the respective sample and reference positions, the method comprising the steps of:
   placing a sample on the sample position;
   measuring sample temperature using the sample temperature sensing means;
   applying heating power over time to each of the sample position and the reference position, the means for controlling solely using measured sample temperature as the basis for determining an amount of the heating power being applied, so as to cause the measured sample temperature to follow a predetermined program of sample temperatures versus time that is configured in the means for controlling; and
   during the step of applying heating power, determining a temperature differential arising between the respective temperature sensing means and deriving a net heat flow into the sample from the temperature differential determined.

2. The method of claim 1, wherein:
   the step of applying heating power is achieved by a PID control loop.

3. A thermo-analytical instrument, comprising:
   a sample position;
   a reference position;
   means for heating each of the sample position and the reference position,
   sample temperature sensing means for sensing a temperature of a sample placed at the sample position;
   reference temperature sensing means for sensing a temperature at the reference position, and
   means for controlling the heating power supplied by the means for heating, the means for controlling comprising:
      a predetermined program of sample temperatures versus time;
      a control loop arranged to apply the predetermined program, by controlling the amount of heating power supplied by the means for heating based exclusively on sample temperature as sensed by the sample temperature sensing means; and
      means for deriving a net heat flow into the sample, based upon a temperature differential arising between the respective temperature sensing means.

4. The instrument of claim 3, wherein:
   the control loop comprises a PID controller.

5. The instrument of claim 3, wherein:
   the sample position and reference position are selected to minimize an imbalance in thermal mass therebetween, when no sample is on the sample position.

6. The instrument of claim 3, wherein:
   the sample position and reference position are selected such that substantially all of a temperature differential arising between the respective temperature sensing means during the predetermined program is due to a sample on the sample position.

7. The instrument of claim 3, wherein:
   the sample position and reference position are thermally separated from each other.

* * * * *